United States Patent
Isola et al.

(10) Patent No.: US 10,537,749 B2
(45) Date of Patent: Jan. 21, 2020

(54) SUPERVISED 4-D DOSE MAP DEFORMATION FOR ADAPTIVE RADIOTHERAPY PLANNING

(71) Applicant: KONINKLIJKE PHILIPS N.V., Eindhoven (NL)

(72) Inventors: Alfonso Agatino Isola, Eindhoven (NL); Davide Fontanarosa, Neerpelt (BE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 158 days.

(21) Appl. No.: 15/501,893

(22) PCT Filed: Aug. 4, 2015

(86) PCT No.: PCT/EP2015/067893
§ 371 (c)(1),
(2) Date: Feb. 6, 2017

(87) PCT Pub. No.: WO2016/023786
PCT Pub. Date: Feb. 18, 2016

(65) Prior Publication Data
US 2017/0232274 A1  Aug. 17, 2017

(30) Foreign Application Priority Data
Aug. 15, 2014  (EP) .................................. 14181156

(51) Int. Cl.
*A61N 5/10* (2006.01)

(52) U.S. Cl.
CPC .......... *A61N 5/1031* (2013.01); *A61N 5/1037* (2013.01); *A61N 5/1045* (2013.01); *A61N 2005/1089* (2013.01)

(58) Field of Classification Search
CPC .................................................... A61N 5/1037
See application file for complete search history.

(56) References Cited

U.S. PATENT DOCUMENTS

| 6,560,311 | B1 | 5/2003 | Shepard et al. |
| 2004/0190680 | A1 | 9/2004 | Chang |
| 2007/0043286 | A1* | 2/2007 | Lu .......................... A61N 5/103 600/407 |

(Continued)

FOREIGN PATENT DOCUMENTS

WO  2009055801 A2  4/2009

OTHER PUBLICATIONS

Wu, J.Q. et al., "On-line re-optimization of prostate IMRT plans for adaptive radiation therapy", Phys. Med. Biol. 53 (2008) 673-691.

(Continued)

*Primary Examiner* — Hoon K Song

(57) ABSTRACT

Method and apparatus (DMS) manage dosage in radiation therapy planning and/or delivery. Images of a region of interest ROI are acquired at different times. A registration transformation is computed that deforms one of the two images into the other. A magnitude of the transformation is then computed based on a suitable metric. If the computed magnitude is found to comply with a pre-defined criterion, the transformation is used to deform a dose distribution map and compute, based on the deformed dose map, therefrom a new fluence map.

7 Claims, 4 Drawing Sheets

(56) References Cited

U.S. PATENT DOCUMENTS

| | | |
|---|---|---|
| 2010/0215147 A1 | 8/2010 | Mueller et al. |
| 2013/0121469 A1 | 5/2013 | Sobering et al. |
| 2016/0279444 A1* | 9/2016 | Schlosser ............. A61N 5/1049 |

OTHER PUBLICATIONS

Plugfelder, D. et al., "A comparison of three optimization algorithms for intensity modulated radiation therapy", Z. Med. Phys. (2008) vol. 18, No. 2, pp. 111-119.

Bortfeld, T. et al., "Decomposition of pencil beam kernels for fast dose calculations in three-dimensional treatment planning", Med Phys. (1993), vol. 20, Abstract.

Zitova, B. et al, "Image registration methods: a survey", Image and Vision Computing (2003), vol. 21, No. 11, pp. 977-1000.

Zhang, Yin et al., "Dose-volume-based IMRT fluence optimization: A fast least-squares approach with differentiability". Linear Algebra and its Applications 428 (2008) 1365-1387.

Lee, T.F. et al., "3D Volumetric Visualization with Automatic Rigid and Deformable Hybrid Image Registration for Adaptive Radiotherapy", Journal of Cancer Science & Therapy, vol. 01, No. 01, Jan. 1, 2009, pp. 041-046.

Flampouri, S. et al., "Estimation of the delivered patient dose in lung IMRT treatment based on deformable registration of 4D-CT data and Monte Carlo simulations" Physics in Medicine and Biology, vol. 51, No. 11, 2006.

\* cited by examiner

SUPERVISED 4-D DOSE MAP DEFORMATION FOR ADAPTIVE RADIOTHERAPY PLANNING

CROSS-REFERENCE TO PRIOR APPLICATIONS

This application is the U.S. National Phase application under 35 U.S.C. § 371 of International Application Serial No. PCT/EP2015/067893, filed on Aug. 4, 2015, which claims the benefit of European Patent Application No. 14181156.2, filed on Aug. 15, 2014. These applications are hereby incorporated by reference herein.

FIELD OF THE INVENTION

The invention relates to a method for dose management in respect of a region of interest, to a dose management apparatus, to a computer program product, and to a computer readable medium.

BACKGROUND OF THE INVENTION

Cancer remains one of the scourges of mankind and radiation therapy is one of the chief tools to combat same. In radiation therapy a high energy treatment radiation beam is used to destroy cancerous tissue whilst sparing healthy one.

A particular type of radiation therapy planning called Intensity Modulated Radiotherapy (IMRT) allows spatially modulating a treatment beam to precisely conform not only in shape but also in terms of prescribed dosage requirements as per a treatment plan.

Standard IMRT implementations do not take into account the eventuality that the anatomy of the treated site may change throughout the course of radiation delivery.

Although in the past some more advanced schemes have been proposed on how to adapt treatment plans to changes in the treated anatomy, the decision on when to adapt still rests with the oncologist. See for instance Q Jackie Wu et al, "On-line re-optimization of prostate IMRT plans for adaptive radiation therapy", Phys. Med. Biol. 53 (2008) 673-691.

But still, in existing schemes, no clues are provided to the human professional on when and/or under what conditions a treatment plan should be re-optimized. The information available to medical personal to reach such a decision may be overwhelming and it may be difficult to draw definite conclusion on how to proceed. This problem is further compounded by the limited resources available to national health services as plan adaptions may prove expensive.

SUMMARY OF THE INVENTION

There may therefore be a need in the art for a method or a related apparatus that supports decision-making in relation to radiation treatment plan adaptation.

It should be noted that the following described aspect of the invention equally apply to the dose management apparatus, to the computer program element and to the computer readable medium.

According to a first aspect of the invention, there is provided a method for dose management in respect of a region of interest, ROI, comprising:
  establishing a spatial registration transformation between a previous image $CBCT_k$ and a current image $CBCT_{k+1}$ of a ROI, the transformation defining a deformation;
  computing a magnitude of said deformation;
  if the magnitude of the deformation complies with a pre-defined deformation criterion or in response to a signal issued in relation to the computed magnitude, applying the registration transformation to an existing dose distribution map $D_k$ for the ROI to obtain a deformed dose map $D_{k+1}$.

According to one embodiment, the method comprises computing a (new, that is, updated) photon fluence vector $\varphi_{k+1}$ based on the transformed dose map $D_{k+1}$.

According to one embodiment, the computing of the fluence vector $\varphi_{k+1}$ includes a least-squares optimization.

According to one embodiment, if the magnitude of the deformation does not comply with a pre-defined deformation criterion, re-computing of an initial dose distribution map $D_0$ is carried out.

According to one embodiment, the method comprises outputting an indication of said deformation magnitude. The indication includes any one or a combination of: i) a visualization or ii) an acoustical signal.

In other words, the proposed dose management method examines the deformation required to bring the current state of the ROI in alignment with a previous state (for instance but not necessarily with the first, initial state). If the deformation is evaluated as not too "severe", the dose distribution map may be deformed according to the deformation experienced by the ROI and a (new) fluence map can be computed by a least square fitting scheme or other suitable numerical technique. In the fitting operation, the new fluence map is fitted to approximate (after multiplication with an updated or an earlier (eg the first) influence matrix) the deformed dose map. This deformation scheme is computationally cheaper than re-computing an earlier (in particular, but not necessarily, the initial fluence map computed at fraction "0") in an expensive re-optimization of the radiation treatment plan (RTP). In this manner a conclusive, rational and definitive decision for treatment plan adaption can be reached. A rerun of a computationally expensive RTP optimization can be reserved for only those cases where the anatomy of the ROI has changed to such an extent that such a rerun is clinically warranted. The severity or magnitude of the deformation can be judged by formulating the criterion (or a combination of different criteria) in terms of suitable, for instance geometrical, metrics, the choice of which being sensitive to the clinical situation at hand. For instance, the criterion may involve computing the Jacobian(s) associated with the transformation to assess whether the transformation is invertible. If the transformation includes a singularity, this may be used as an indication that the (anatomical) change of the ROI since the original RTP was set up is substantial and that a re-computation of the RTP is advisable.

The computed deformation magnitude may be used as a token on the accuracy or fidelity of how closely the so deformed dose map would stay true to the prerogatives of the treatment plan.

The signal in relation to the computed deformation magnitude for going ahead with the deformed dose map may be user issued for instance after visualizing the deformation magnitude on the monitor to the human user. If the user believes the criteria are met, he or she issues the signal as a confirmation signal by mouse click or keyboard event or otherwise so that the adaptation of the current or earlier fluence map based on the deformed dose map can be carried out. If the deformation magnitude is evaluated as too high or as too severe, the user can request instead a new RTP optimization. A rerun of the RTP optimization may then require acquisition of a new initial image.

However, in an alternative, fully automatic embodiment the signal may be automatically issued by a decision logic (after evaluation of the transformation magnitude against the pre-defined criterion) so no user issued confirmation signal is necessary.

The images may be 3D CT images though this may not necessarily be so as imagery from other modalities and/or lower dimensional imagery may also be used in some embodiments.

Herein, the term "ROI" is used to indicate a target site, that is, that part of the body that is to be treated with radiation such as a tumor, pockets of cancerous tissue etc.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
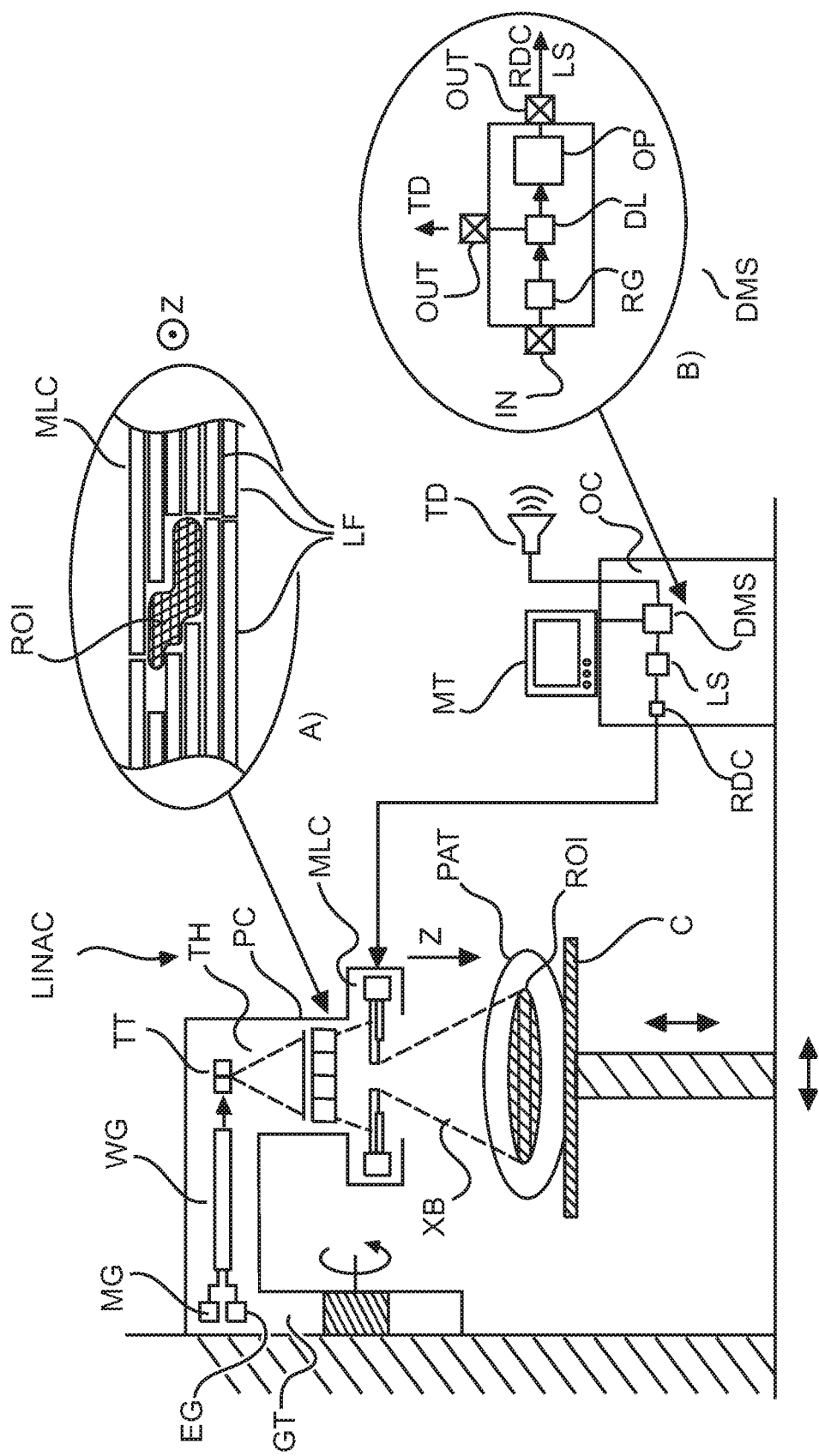
FIG. 1 shows an arrangement for radiation delivery.

With reference to FIG. 1, there is shown an arrangement for delivering radiation in radiation therapy. The main goal in radiation therapy is to kill off cancerous tissue ROI in an animal or human patient PAT. More particularly the objective is to kill off as much of the cancerous tissue as possible but at the same time to spare as much of the healthy tissue as possible that surrounds the cancerous tissue.

A high energy x-ray treatment beam XB is radiated across the cancerous tissue ROI, preferably from a number of different angles.

Radiation therapy is achieved by using a linear accelerator system (referred to herein as "LINAC"). The LINAC system is to be used for IMRT. The LINAC comprises a rotatable gantry GT. The gantry is rotatable around a treatment region and around one or more axis. Only one rotation axis is shown in FIG. 1 (see the rounded arrow) but this for illustrative purposes only and in no way limiting as the LINAC may include more than one axis of rotation. In the treatment region the patient PAT to be treated is deposited on a treatment couch C.

The rotatable gantry includes a treatment head TH. In one embodiment, the LINAC further includes an electron gun EG, a magnetron MG and a wave guide WG. The waveguide WG is directed from the electron gun towards a tungsten target TT.

In operation, electron gun EG injects a flow of electrons into the wave guide WG. The electrons are accelerated by microwaves generated by the magnetron MG as the microwaves travel through the wave guide. The accelerated electrons impact on the tungsten target TT. This impact causes a high energetic x-ray beam to be formed. This primary x-ray beam may be collimated by a primary collimator PC arranged in the treatment head to reduce scatter. The components of the LINAC as summarized above are purely for illustrative purposes and are not limiting. In particular, other LINAC designs are likewise envisaged herein.

The so pre-collimated treatment beam then passes through a multi leaf collimator MLC arranged after the primary collimator in the treatment head TH. The multi-leaf collimated treatment beam XB then egresses the treatment head TH, travels through the treatment region and is then projected through the patent PAT and in particular through the region of interest ROI to ideally destroy all of the cancerous tissue.

One function of the multi leaf collimator MLC is to provide shaping of a cross section of the treatment beam so that the cross section at least roughly conforms to the geometric structure of the ROI. Another, more important function of the MLC for IMRT purposes is to position the leaves LF in the beam to form a plurality of openings to locally modify parts of the beam to so effect the desired radiation intensity modulation for IMRT.

Inset A) of FIG. 1 affords a view on the multi leaf collimator MLC along the projection direction Z, that is, along the propagation direction of the beam XB (in inset A), the projection direction Z extends into the paper plane). As can be seen, the multi-leaf collimator MLC is formed from a plurality of opposing pairs of highly radio-opaque, elongate structures, namely the leaves or blades LF. The opposing leaves are moveable by suitable actuators independently from each other. One or more openings can be formed anywhere within the beam's cross section between opposing pairs of leaves. Because of the leaves being independently movable and by employing a sufficient number (sometime 30 or more although this is no way limiting) of leaf pairs with each leaf of sufficient thinness (about 5 mm), a complicated pattern of openings can be formed.

In one embodiment the MLC also includes a number of dedicated beam blocking means (sometimes referred to as "jaws") through which the overall beam shaping is effected. For instance, the MLC may have a set of N leaves and for instance a number of jaws (for instance four but this is for illustration only and in no way limiting). The jaws are arranged in opposing pairs at north, south, west, east direction relative to the beam. For each beam direction (that is for a given treatment head position), the jaws' positions are aligned from each side as close as possible to the contour of the ROI as per said direction. This defines a reduced (for instance, but not necessarily, a square shaped) area, also called "active area", which is left open. Structures (such as the ROI) within this area can then be exposed to beam irradiation. Structures outside the active area (that is, "behind" the jaws) will not be irradiated. This reduces (or may even cancel) unwanted extra dose to the surrounding organs at risk.

Overall control of the LINAC's operation is from an operation console OC or work station communicatively coupled to the electronics of the LINAC system. The operation console OC may also include a control monitor MT. The operator console runs a dose supervisor or management module DSM, whose operation will be explained in more detail below at FIG. 4. Broadly, the dose management module DSM is configured to modify components of a radiation treatment plan. If certain conditions are found to be fulfilled, the modified treatment plan may be passed on to a leaf sequencing tool LS that translates the treatment plan into control commands in particular for the multi-leaf collimator and/or the activation of the X-ray beam XB and/or motion of the gantry to position the treatment head TH along the required direction. The control commands are then forwarded to radiation delivery controller RDC who then sends out corresponding lower level position commands to the MLC so that the collimator leafs assume suitable positions to form the necessary openings for carrying into effect the intensity modulation of the beam. The RDC controller may also be in charge to active the beam and to position the treatment head TH along the required direction relative to the ROI.

A radiation therapy plan includes in particular a quantity known as a "fluence map". The fluence map cp defines the intensity of the treatment beam across its cross section. More particularly, a treatment beam (also called an elementary beam), for a given radiation direction (as per the treatment head's position relative to the ROI) is comprised from single rays called "beamlets". Each elementary beam is determined by its angular position (or direction $\alpha$), its initial energy and its (2D) fluence map $\varphi_i$. The fluence map comprises elements called bixels. The number of "bixels" in each fluence map is equal to the number of beamlets for the given elementary beam. Each bixel defines a "weight" (that is, a number) for a particular beamlet. This weight expresses the contribution of said beamlet to the dose delivered along said direction. In IMRT then, the total irradiated dose is composed by the superposition of several independent elementary beams, one static beam per each angular direction. Usually, between 5-14 (but this number is exemplary only) delivery directions are used in IMRT.

Given a set of suitably optimized "ideal" fluence maps (intensity profiles) obtained from a fluence map optimization (FMO—on which more below at FIG. 4), the leaf sequencing tool LS part takes care to specify the required MLC openings as defined by the MLC leaf positions and, if present, jaw positions. The intensity profiles will be non-zero only within the active area left opened by the jaws. The summation of all delivered MLC openings is then expected to reproduce in sufficient accuracy the intensity profiles (as per the "ideal" fluence maps) within the "active area". Each single MLC opening can produce a beam cross-section which can be different (in particular smaller) from the ROI's area along the given projection. Any of a number of different leaf sequencing techniques such as step-and-shoot or "sliding window" can be used, all of which are envisaged herein.

In conclusion, the multi leaf collimator affords a spatial intensity modulation of the x-ray beam to thereby realize a spatial intensity profile as required by the fluence map. The ability of spatially modulating the beam's intensity is the essence of IMRT which helps further the objective of killing of as much of the cancerous tissue and sparing as much of the healthy tissue as possible.

Figure 2:
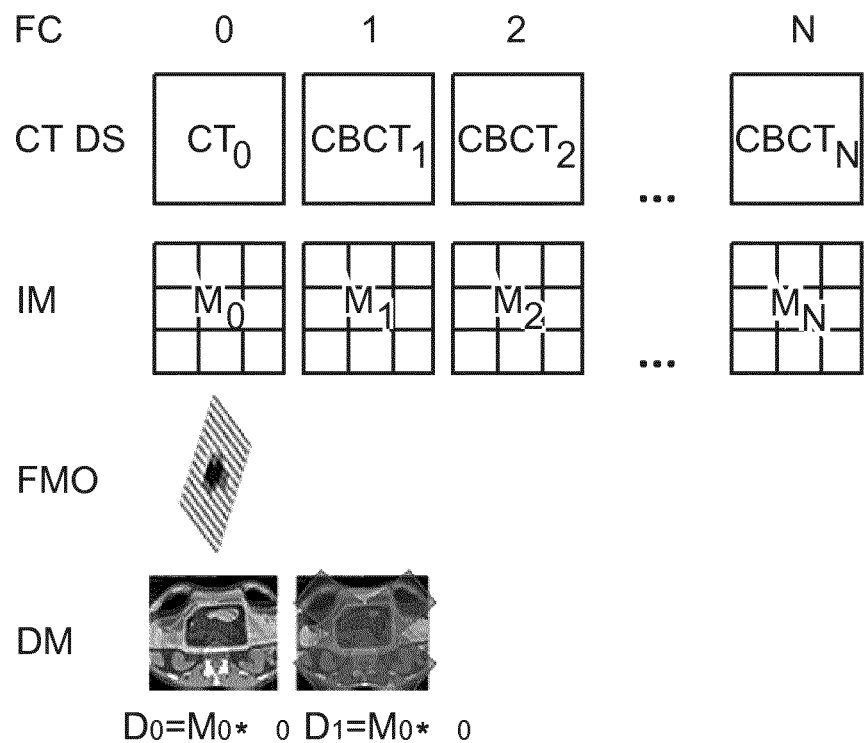
FIG. 2 shows a block diagram of a radiation therapy scheme.

With reference to FIG. 2 there is shown an overview of a non-standard radiation treatment procedure. The treatment plan mentioned earlier also includes a quantity known as a (3D) dose (distribution) map D. The dose map D defines the overall x-ray dosage to be administered to different portions of the ROI. Usually the treatment extends over different periods of time, that is, parts of the total dosage are delivered as fractions k=0 through k=N at different points in time. The fractions may be delivered hourly, daily or weekly or at in other suitable time periods. Also, for any given fraction, the dosage may be delivered at different projection directions. Based on clinical requirements, an initial fluence map $\varphi_0$ is computed. This is usually based on an initial computed tomography (CT) image $CT_0$ acquired of the ROI at commencement of the treatment. For each fraction k instance, an influence matrix M is computed. The influence matrix M allows computing the dose D map due from the fluence map as per a matrix multiplication $D=M \cdot \varphi$. In this matrix multiplication notation, each entry of the influence matrix M represents the delivered dose per unit fluence. Also, for notational efficiency, $\varphi$ denotes a "global" fluence map vector that includes "lined up" the individual fluences $\varphi_\alpha$, for all beam directions $\alpha$.

The influence matrix $M_k$ for a given fraction k is based on an updated CT image taken of the ROI before each fraction k. This "image of the day" $CBCT_k$ reflects the current state of the region of interest ROI. The image of the day may be a cone beam CT image or an ultrasound (2D or preferably 3D ultrasound) image or may be acquired by any other suitable imaging modality such as magnetic resonance (MR), etc. The image of the day $CBCT_k$ is then used to compute in a known manner the influence matrix M associated with the current state of the ROI. From the updated influence map $M_k$ and the initial fluence map $\varphi_0$, an updated dose map $D_k$ can be computed, as mentioned, by matrix multiplication. The dose map $D_k$ describes, in light of the changes as recorded in the image of the day, the dose that must be delivered locally across the different portions of the ROI in the fraction k, based on initial fluence $\varphi_0$. In other words, the computation of the dose map $D_k$ for fraction k>0 is still based on the initial fluence map $\varphi_0$. The determination of the initial fluence map requires extensive computations so one tries to avoid re-computing the fluence map $\varphi_0$ for each of the follow-up fractions. However, due to, for instance, changes in the region of interest, the dose map may substantially deviate from what is described in the treatment plan. This is unsatisfactory and the proposed method and supervisor module DMS as proposed herein helps to cope with the dynamics of the region of interest whilst taking into account the expenses associated in re-computing $\varphi_0$ in a new plan optimization.

Figure 3:
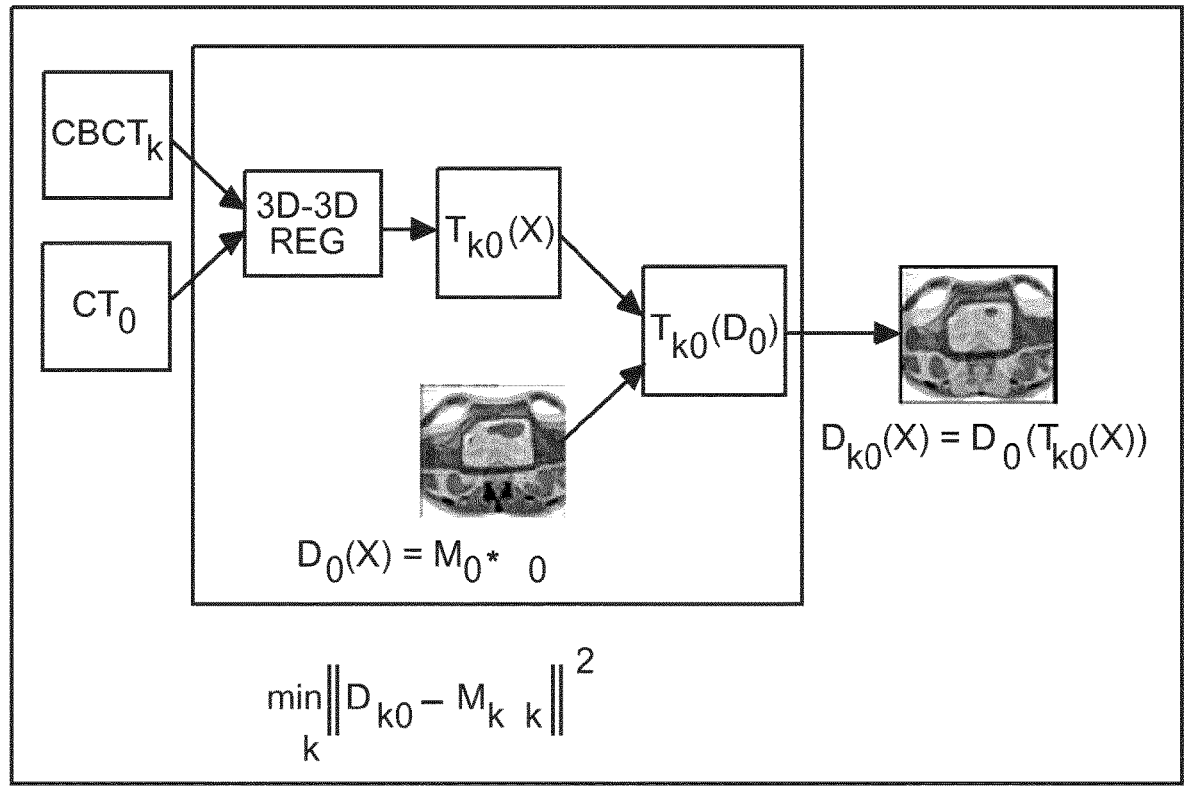
FIG. 3 shows a block diagram of a dose distribution adaption.

With reference to FIG. 3 there is shown a block diagram which summarizes operation of the proposed supervisor module DMS. What is proposed herein is that for each or at least a single or a subset of fractions k>0, a deformation field $T_{k0}$ is computed. The deformation field is derived from a registration of the initial CT image to the current CT image $CBCT_{k0}$ acquired at the k-th fraction. This deformation field $T_{k0}$ is then used to deform the initial dose map $D_0$ derived from the initial influence matrix $M_0$ and the initial fluence map $\varphi_0$. This deformed dose $D_{k0}$ map is then used as a target dose map to compute in an optimization procedure an updated fluence map $\varphi_{k0}$, if the deformation field $T_{k0}$ is found to comply with a predefined criterion/criteria. The computation (if the criterion is fulfilled) can be done by least square optimization or other suitable numerical technique. The updated fluence map $\varphi_k$ is computed to approximate the deformed dose map $D_{k0}$ when applied to the current influence matrix $M_k$ for the considered fraction.

Broadly, and as shown in inset B) of FIG. 1, the supervisor module DMS as proposed herein includes an input port IN and an output port OUT. The radiation controller RDC includes a registration module RG, a decision logic DL and an optimizer module OP. The registration module RG computes the deformation field required to register the initial CT image to the one acquired at fraction k. The transformation field so computed is then applied, if the decision logic DL so decides, to the current dose map as explained above to derive a deformed one from which in a simplified optimization scheme a new updated fluence map is computed. As proposed herein, before the transformation field is applied to the current dosage map, the decision logic DL examines the transformation field and checks whether it complies with the pre-defined criteria. If the transformation field does not comply with the pre-defined criteria an alert signal is issued to a transducer TD to alert the user to the fact that the underlying transformation field is "too severe" in nature. The alert signal may be used to activate an alert lamp or to issue an acoustic alert signal or similar. The alert signal may also be used to initiate or recommend a re-computation of a new, initial fluence map in the computationally expensive plan optimization. Otherwise if the transformation field is found to comply with the pre-defined criteria flow control passes on to optimizer to instruct same to adapt for a new fluence map as explained above in FIG. 3. In other words a computationally expensive re-computation of $\varphi_0$ can be avoided in some cases and is done only if necessary, that is, when the deviations of the ROI from its initial state at k=0 are substantial because the deformed ROI would necessitate a dosage map that substantially departs from the initial treatment plan.

Figure 4:
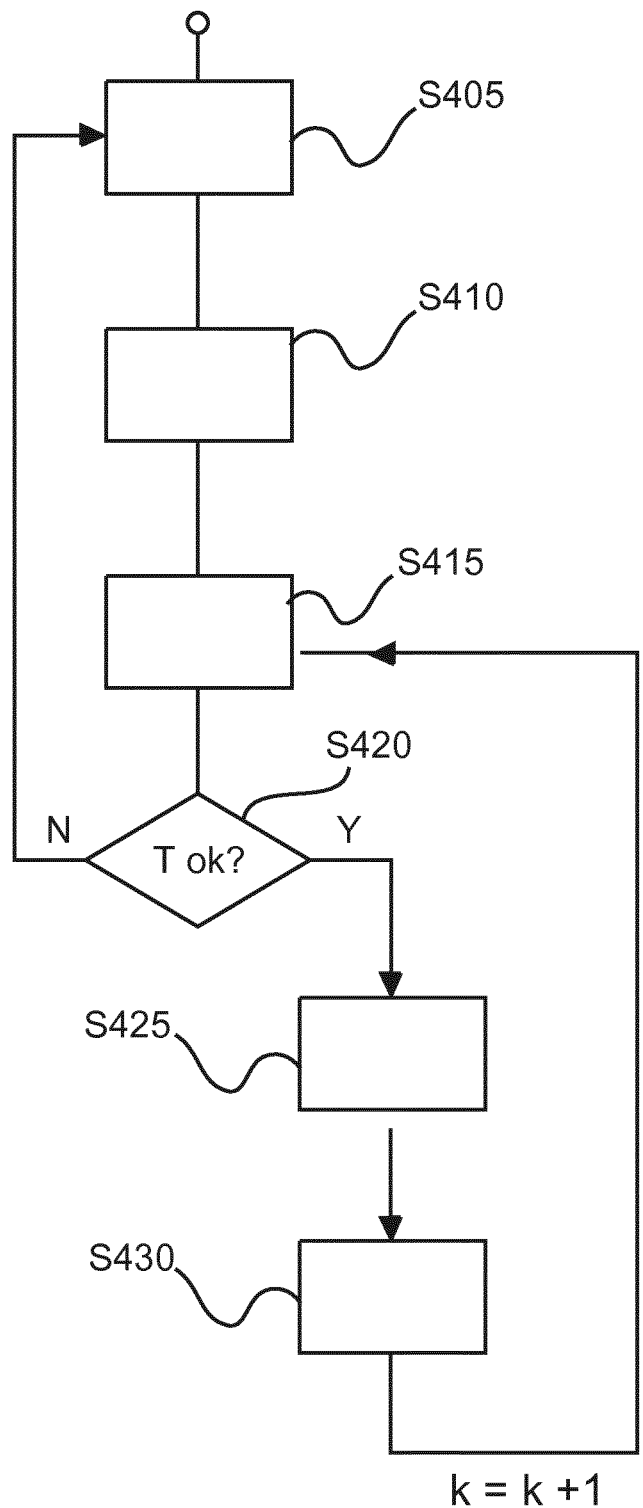
FIG. 4 shows a flow chart of a method for adapting a treatment plan.

With reference to the flow chart in FIG. 4, a method for dose management for improved radiation delivery will now be explained in more detail.

At a preliminary step S405, an initial RTP optimization is carried out, that is an initial fluence map optimization (FMO) is determined at fraction 0.

At the first fraction 0, the following is given: an initial CT image $CT_0$ of patient PAT, a, in one embodiment, composite dose objective functional $f(\varphi)$ and a dose influence matrix $M_0$ are given. The functional objective $f$ "encodes" anatomy sensitive, clinical dose requirements and is defined on the space of fluence maps $\varphi$. The plan optimization can be understood as a constrained optimization problem with the functional f defining said constraints on the fluence maps space of $\varphi$. The functional $f$ is "composite" in the sense that it expresses multiple optimization objectives and the optimization requires minimizing their weighted sum, the so called composite cost function. Also, as opposed to the various "images of the day" for the different fractions k>0, it has been observed that cone beam CT is not accurate enough so a (full) non-cone bone (eg parallel or fan) beam CT scanner or MR (or any other modality capable of delivering imagery at the required accuracy/resolution is also envisaged) or 3D ultrasound is used for the initial image.

The influence matrix is a rectangular matrix n×m, consisting of all m beamlets contributions to all n voxels of the volume to be irradiated. Hereto, an optimized 2D fluence map $\varphi_0$ for each IMRT beam angle is determined by minimizing the functional $f(\varphi)$, and the corresponding 3D dose distribution $D_0(x)=M_0 \varphi_0$ is computed, where x=(x,y,z) is a point in the volume grid. In other words matrix-multiplying M with $\varphi$ yields a 3D volumetric dose distribution D of the dose over points $\underline{x}$ in patient's body. More explicitly D(x) =M(x,b)·$\varphi$(b), where x is the spatial grid position and b is a beamlet index.

The 2D target fluence map for each treatment beam angle $\varphi_0$ is calculated by solving a positivity-constrained optimization problem with known methods. See for instance Pflugfelder et al, "A comparison of three optimization algorithms for intensity modulated radiation therapy", Z. Med. Phys. (2008) Vol. 18, No. 2, pp. 111-119.

In one exemplary embodiment of the plan optimization, the ROI is firstly delineated and segmented based in image information as per initial image $CT_0$. In the RTO optimization, an objective $f(\varphi)$, which is function of the dose distribution in the target, is optimized to deliver the desired IMRT plan. The corresponding 3D optimized dose distribution can be determined as $D_0(x)=M_0 \varphi_0$, where x=(x,y,z) is a point in the volume grid.

At preliminary step S410, the dose distribution for a fraction k is evaluated based for instance on patient PAT's CBCT of the day ($CT_k$) and, in one embodiment, a new influence dose matrix $M_k$ is computed. Again, using cone beam CT for acquiring the image of the day $CT_k$ is according to one embodiment only. In another embodiment, a US (2D or, preferably, 3D) image is used instead but an MR or other imaging modality may likewise be used with benefit.

For computing the new influence dose matrix $M_k$, well known "dose engines" can be applied to determine the new dose influence matrix such as thin pencil beam (TPB)-based, SVD (singular value decomposition) TPB-based, collapse cone-based, Monte-Carlo-based dose engines, etc. See T. Bortfeld et al., "Decomposition of pencil beam kernels for fast dose calculations in three-dimensional treatment planning", Med Phys. (1993), Vol. 20, pp. 311-8 and references therein. Finally, the volumetric dose distribution at fraction k can be computed as $D_k(x)=M_k \varphi_0$. If this 3-D dose distribution satisfies all or at least some clinical requirements then the plan can be readily delivered. But, if due to geometrical misalignments and/or to anatomical changes in respect of the ROI (e.g., the tumor has shrunk due to the RT curative action, or some new features have appeared within the region of interest), the new dose distribution $D_k$ may not be acceptable for delivery, and then a new lengthy and costly RTP optimization (to determine a new optimized fluence map $\varphi_k$) or some kind of plan adaption may be called for.

The following steps furnish a proposed solution as to how to cope with such ROI dynamics in a computationally economical way.

In step S415, the image registration is carried out by registration component RG of dose supervisor module DMS. The rationale for this step is as follows. In cases were no anatomical changes and geometrical misalignment occur, the dose distribution at each k-th fraction $D_k=M_k \varphi_0$ will be identical to the original dose map $D_0$. But, if volume changes do happen, the original beamlets as per $\varphi_0$ would create a dose distribution $D_k(x)$ which is different from the expected one. If we assume that only a moderate anatomical change took place between 0-th and k-th fractions, it may be likewise assumed that the dose distribution could "follow" or co-vary with these anatomical changes so a "co-geometrically" deformed dose can be expected to resemble the desired dose at treatment. A plethora of rigid and elastic registration methods have been proposed to correct for geometrical misalignments. See for instance B. Zitová, J. Flusser, "Image registration methods: a survey", Image and Vision Computing (2003), Vol. 21, No. 11, pp. 977-1000 and references therein. In case a simple roto-translation of the couch is not enough to correct for anatomy differences, system setup and/or couch positions errors, a more sophisticated rigid and/or elastic (or optical flow-based) registration method can be applied to correct for the misalignment. In order to determine the desired deformation field, the current reconstructed CBCT image $CT_k$ is registered in instant step S415 to the initial CT image of the first fraction $CT_0$. In alterative embodiments, registration is into an earlier $CT_{l(l<k)}$ image, not necessarily onto the initial one. In cases where $CT_0$ and $CT_k$ images are given at different spatial resolution, an additional grid resampling will be required before starting registration (e.g. tri-linear interpolation). The outcome of this registration step is a 3D deformation field $T_{k0}(x)$ each of its entries describing the local rigid and/or elastic changes required to deform the two considered images into each other.

In step S420, a magnitude of the deformation is validated for accuracy or acceptability. Exact image registration can be very difficult (e.g. for lungs RT), especially in those cases where significant changes of the anatomy occur. In these cases due to potential non-invertible folding motion patterns some unwanted events could take place during registration (e.g., creation/annihilation of voxels).

In order to increase safety, and help decision making, or more statistics or metrics of the deformation field $T_{k0}$ is determined in step S420. The statistics or metrics may then be returned to the user as a feedback for instance as a visual rendering or other signal. A user specified or otherwise pre-defined criterion such as a threshold for, in one embodiment, the maximum and/or average magnitude of the entries of the deformation field $T_{k0}$ could be used to detect strong deformations within the field (strong deformations could lead to very inaccurate deformed dose distributions).

According to one embodiment, the metric is computed as the Jacobian matrix $J_T$ of the deformation field $T_{k0}$ to identify points with potential non-invertible motion patterns. The determinant of the Jacobian could be used to deliver a color-coded 3D map showing said points with potential non-invertible motion patterns. In this embodiment the threshold is set up in respect to the determinant values.

In other words, the computed metric furnishes an image based similarity measure on how similar the ROIs are as per the current image of the day and a previous image (for example the initial image), or, in yet other words, the metric serves as an indication on a quality measure of the performed registration.

The computed magnitude of the deformation/registration transformation is then compared by the decision logic DL against the threshold. If the magnitude is judged to comply with the predefined criterion, flow control passes on to step S425, either automatically or after receiving a confirmation signal from the user. The magnitude evaluation may take the form of comparing whether the computed metric is below or above the threshold. For instance this may be done by comparing the maximum and/or average magnitude (eg, a length) of vector entries of the deformation field $T_{k0}$ against the threshold. If essentially all (safe for a pre-defined number of outliers) of the vector entries are below the threshold, this may indicate the deformation field $T_{k0}$ is acceptable so the current structure/position of the ROI is sufficiently similar to its previous in particular initial structure/position.

Alternatively or in addition it may be checked whether the transformation at one or more ROI grid points is invertible by checking its Jacobian determinant as briefly mentioned above. The transformation $T_{k0}$ is deemed acceptable if the transformation is invertible (i.e, non-zero Jacobian determinant). To be more specific, as the determinant of the Jacobian is continuous in the spatial domain and as regions of identity transformations (i.e., non-moving/changing areas, where the determinant returns unity) are possible, the determinant of the Jacobian matrix must be strictly positive. Therefore, in one embodiment, the transformation $T_{k0}$ is deemed acceptable only if the determinant of the Jacobian is positive ($>0$) at all positions x in the ROI or if the number of positions x with determinant of the Jacobian non-positive is less than a pre-defined critically threshold.

If, however, it is evaluated that the deformation field $T_{k0}$ does not comply with the criterion, for instance, if the maximum and/or average magnitude of the entries of the deformation field $T_{k0}$ exceed the threshold at more than a pre-set number of positions and/or there is at least one ROI grid point at which the transformation is non-invertible as per the Jacobian test embodiment, this is flagged up as the transformation being not acceptable. Flow control may then return to step S405 to re-optimize for a new RTP based for instance on a new CT image.

Referring now back to the Jacobian test, it has been found that the presence of non-invertible deformation (that is, the Jacobian is zero or is negative at at least one point x or at more than a predefined number of points x in the ROI) may indicate significant anatomical changes so that a re-run of the plan optimization as per S405 may be warranted although said step S405 is expensive in terms of resources. In other words, in the embodiment where the Jacobian test is used, a transformation field $T_{k0}$ will be deemed as unacceptable if there is at least one position x (or if there are more than a pre-set number ($>1$) of positions x) for which the determinant of the Jacobian is negative ($<0$) or zero.

The fact that the transformation is not-acceptable may be indicated to the user either visually or acoustically by driving a suitable transducer TD such as a flash lamp or a loudspeaker. Visual indication may also include displaying suitable information on the monitor MT to the user, eg, a visual rendering of the metric, eg by showing a visual diagram with positions x are highlighted where the vector field violates the pre-set magnitude criteria or where the Jacobian indicates non-invertibility (singular points), etc.

At step S425, if the deformation field is found to satisfy the criteria, the deformation field $T_{k0}$ is applied to deform the initial dose map $D_0$ to the current image of the day $CT_k$. The outcome of this step is a new, correspondingly "deformed" dose map $D_{k0}(x)=D_0(T_{k0}(x))$. Alternatively, the deformation may be applied to a previously approved or otherwise suitable dose Map $D_0$.) so may not necessarily be applied to the initial dose map $D_0$.

At step S430, a fluence map adjustment is carried out. In order to determine the new beam fluence profiles $\varphi_k$ (which can deliver the desired deformed dose distribution $D_{k0}$), the pseudo-inverse of matrix $M_k$ is computed in one embodiment to yield $$\varphi k = M_k^{-1(pseudo)} \cdot D_{k0}$$

Alternatively, for instance if this matrix inversion is not easily practicable, a least square problem can be solved instead to determine the updated fluence maps $\varphi_k$. Here, a least square fluence map optimization (FMO) problem is solved by optimizer OP to find the best beamlet fluence intensities $\varphi_k$ which can deliver a dose map $D_k^{opt}$ similar (or as similar as possible as measured relative to a chosen norm ||) to the reference deformed dose map $D_{k0}$:

$$\hat{\varphi}_k = \min_{\varphi k} \| D_{k0} - M_k \varphi_k \|^2 \tag{1}$$

Here, in order to find an optimal solution, common quadratic convergent non-linear unconstrained optimizers (e.g. conjugated gradient, L-BFGS) can be applied. See for instance the Pflugfelder reference cited earlier. Closeness may be measured against any suitable norm || and "best" or "as similar as possible" may not necessarily mean "best" or "most similar" in the absolute sense but in some embodiments "closeness" within a pre-defined margin may be sufficient to establish the new updated fluence map.

In one embodiment, rather than re-computing $M_k$ via dose engines (although can still be done in other embodiments), in the optimization (1) approach we assume $M_k=M_0$, that is, we approximate $M_k$ for follow up fractions k by the initial dose influence matrix $M_0$ obtained in the initial optimization step S405. This assumption is borne out by the observation that the changes of M (the influence matrix) that may be caused by anatomical changes in the ROI are negligible for certain cancer sites, such as prostate and it is assumed herein that this assumption is valid for other cancer types as well.

Steps S415-S430 may now be iteratively executed until the maximum number of fractions is reached. In other words, the above deformation and deformation supervision may be repeatedly applied on a fraction-by-fraction basis for each k although this may not be so necessarily as the method may be applied only at a single fraction k>0 or only at some fractions, eg, for every other fraction or every m-th (m>2) or at random etc.

In yet other words, if the transformation is accepted, the plan does not need to be re-optimized as per step S405, but it is merely enough to adapt the fluence map to the deformed dose map as per step S430 which is computationally less expensive than step S405. In the adaptation as per step S430, the deformation of dose map is "carried over" to new fluence map. Put differently, in step S430 the fluence map is merely co-deformed with the deformed dose map. No "re-computation" of the fluence map from "scratch" as in step S405 is required. In particular, the computationally expensive dose computation part as per plan optimization of step S405 for the initial fluence map $\varphi_0$ can be avoided. Plan optimization step S405 is also expensive because the computations need be based on a new, updated CT image and the new plan needs to be approved by an authorized human expert. In particular, based on the CT a new influence matrix needs to be computed, one needs to re-segment for the ROI, set up again all the dose constraints whilst taking into account the already delivered dose at previous fractions, etc. This can be very tedious, expensive and time consuming. In this situation, the prosed method allows a rational basis for avoiding the re-optimization and to perform instead the relatively "cheap steps" S425-430 to find the modified the fluence maps.

The proposed method may be particularly useful in clinical cases where moderate geometrical and anatomical differences occur, where the proposed method could improve the accuracy of the total delivered dose over multiple IMRT treatment fractions. Moreover, to increase safety and trust, the feedback on the accuracy current dose correction as per step S is provided to the planner.

The method proposed herein is suitable for IMRT but may also be used in VMAT (volumetric modulated arc therapy). When VMAT is used, the leaf sequencing step will need to be adapted to account for the continuous rotation of the treatment head during radiation delivery which is different from IMRT where the radiation delivered (as mentioned above) in a pre-set number of static elementary beams from discrete directions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A radiotherapy method with dose management in respect of a region of interest (ROI), comprising:
 a) generating a first diagnostic planning image ($CBCT_k$) of a region of interest including a target zone to receive radiation therapy;
 b) determining from the first diagnostic planning image ($CBCT_k$) a first radiotherapy plan which controls a radiation source to irradiate the region of interest to deliver a first dose distribution ($D_k$) to the ROI;
 c) performing a first radiation therapy fraction using the first radiation therapy plan to control the radiation source to deliver the first dose distribution ($D_k$) to the ROI;

d) in preparation for a second radiation therapy fraction, generate a second diagnostic planning image ($CBCT_{k+1}$);

e) establishing a spatial registration transformation between the first diagnostic planning image ($CBCT_k$) and the second diagnostic planning image ($CBCT_{k+1}$) of a ROI, the spatial registration transformation defining a deformation ($T_k$);

f) computing a magnitude of said deformation ($T_k$);

g) compare the magnitude of the deformation with a pre-defined deformation criterion;

h1) in response to the magnitude failing to comply with the pre-defined deformation criterion, repeating steps a) and b) to determine a second radiation therapy plan and performing the second radiation therapy fraction based on the second radiation therapy plan;

h2) in response to the magnitude complying with the pre-defined deformation criterion, applying the spatial registration transformation to a map of the first dose distribution ($D_k$) for the ROI to obtain a map of a second dose distribution ($D_{k+1}$);

i) deliver the second dose distribution ($D_{k+1}$) to the ROI; and j) perform the second radiation therapy fraction by controlling the radiation source to deliver the second dose distribution ($D_{k+1}$) to the ROI.

2. The method of claim 1, further including:
outputting an indication of said deformation magnitude.

3. The method of claim 2 wherein the indication includes any one or a combination of: i) a visualization or ii) an acoustical signal.

4. A radiation therapy system with dose management comprising:
a radiation source;
a diagnostic imaging system configured to generate diagnostic images (CBCT) of a region of interest (ROI) including a target zone to receive radiation therapy;
one or more data processors configured to:
determine a first radiotherapy plan which controls a radiation source based on a first diagnostic image ($CBCT_k$) to deliver a first dose distribution ($D_k$) to the ROI;
control the radiation source to perform a first radiation therapy fraction using the first radiation therapy plan to control the radiation source to deliver the first dose distribution ($D_k$) to the ROI;
in preparation for a second radiation therapy fraction, control the diagnostic scanner to generate a second diagnostic image ($CBCT_{k+1}$);
establish a spatial registration transformation between the first diagnostic image ($CBCT_k$) and the second diagnostic image ($CBCT_{k+1}$) of the ROI, the transformation defining a deformation ($T_k$);
compute a magnitude of said deformation; and
apply the registration transformation to an existing dose distribution ($D_k$) for the (ROI) to obtain a deformed dose distribution ($D_{k+1}$);
if i) the magnitude of the deformation complies with a pre-defined deformation criterion or ii) in response to a signal issued in relation to the computed magnitude, control the radiation source to deliver the deformed dose distribution to the ROI; and
if the magnitude fails to comply with the pre-defined deformation criteria, generating a new diagnostic image and a new radiation therapy plan based on the new diagnostic image and control the radiation source to perform the second radiation therapy fraction by controlling the radiation source to deliver a second dose distribution ($D_{k+1}$) to the ROI in accordance with the new radiation therapy plan.

5. The system of claim 1 wherein the radiation source includes a linear accelerator (LINAC).

6. A non-transitory computer-readable medium having stored thereon computer software configured to control a data processor of a radiation therapy system to perform the method of claim 1.

7. A radiation therapy system including one or more computer processors configured to:

a) receive a first diagnostic image of a region of interest of a subject and use the first diagnostic image to generate a first radiation therapy plan which identifies a first dose distribution to be delivered to the region of interest and in a first fraction control a radiation source to deliver the first dose distribution to the region of interest;

b) for a subsequent fraction, receive a second diagnostic image;

c) register the second diagnostic image with the first diagnostic image to determine a deformation therebetween;

d) compare a magnitude of the deformation with a pre-defined deformation criterion;

in response to the magnitude of the deformation failing to meet the preselected criterion, generating a new diagnostic image and determining a new radiation therapy plan using the new diagnostic image with a second dose distribution, and in response to the magnitude meeting the pre-defined criterion, applying the determined deformation to a map of the first dose distribution to generate a transformed dose distribution, and e) control a radiation source to deliver the second dose distribution or the transformed dose distribution to the region of interest during the subsequent fraction.

* * * * *